United States Patent [19]

Dany et al.

[11] Patent Number: 4,931,272

[45] Date of Patent: Jun. 5, 1990

[54] TOOTH PASTES, CLEANING AGENT FOR TOOTH PASTES BASED ON DICALCIUM PHOSPHATE-DIHYDRATE, AND PROCESS FOR MAKING SUCH CLEANING AGENT

[75] Inventors: Franz-Josef Dany; Horst Klassen, both of Erftstadt; Renate Adrian; Hedwig Prell, both of Hürth; Gerhard Kalteyer, Erftstadt, all of Fed. Rep. of Germany

[73] Assignee: Hoechst Aktiengesellschaft, Frankfurt am Main, Fed. Rep. of Germany

[21] Appl. No.: 154,957

[22] Filed: Feb. 10, 1988

[30] Foreign Application Priority Data

Feb. 24, 1987 [DE] Fed. Rep. of Germany ....... 3705845

[51] Int. Cl.$^5$ .......................... A61K 7/16; C01B 25/32
[52] U.S. Cl. ........................................ 424/49; 106/35
[58] Field of Search .............................. 424/49; 106/35

[56] References Cited

U.S. PATENT DOCUMENTS

| | | | |
|---|---|---|---|
| 4,002,732 | 1/1977 | Gault | 424/49 |
| 4,118,471 | 10/1978 | Pensak | 424/49 |
| 4,716,034 | 12/1987 | Schelm | 424/49 |
| 4,728,508 | 3/1988 | Hayes et al. | 424/49 |
| 4,765,984 | 8/1988 | Vellekoop et al. | 424/49 |

FOREIGN PATENT DOCUMENTS

| | | |
|---|---|---|
| 0017784 | 10/1980 | European Pat. Off. |
| 0040938 | 12/1981 | European Pat. Off. |
| 2648061 | 4/1978 | Fed. Rep. of Germany |
| 1548465 | 7/1979 | United Kingdom |

*Primary Examiner*—Nathan M. Nutter

[57] ABSTRACT

Tooth pastes contain a cleaning agent consisting of dicalcium phosphate-dihydrate. The cleaning agent has an adsorptive power of more than 60 g $H_2$/100 g. Disclosed is the cleaning agent and a process for making it.

7 Claims, No Drawings

TOOTH PASTES, CLEANING AGENT FOR TOOTH PASTES BASED ON DICALCIUM PHOSPHATE-DIHYDRATE, AND PROCESS FOR MAKING SUCH CLEANING AGENT

Dicalcium phosphate-dihydrate (DCP-D) and anhydrous dicalcium phosphate (DCP-A) are compounds which have long been used as cleaning agents in tooth pastes. The DCP-D/DCP-A-grades have remineralizing properties—their ionic constituents are practically the same as those contained in dental enamel—which they combine with the property of imparting excellent cleaning and polishing effects to tooth pastes made therefrom. The fact that DCP-A has an abrasiveness approximately 7 times that of DCP-D makes it possible for the cleaning power and polishing activity to be adapted to requirements by using an appropriate composition of the two cleaning agents. Preference is however given to the use exclusively of DCP-D as it complies with the most relevant specifications a modern cleaning agent for tooth pastes has to comply with. It is however required to be used in admixture with DCP-A especially for removing tenaciously adhering matter, such as smoke fur. The use of DCP-D/DCP-A-compositions has also been suggested and tried in so-called antiplaque pastes.

The properties of DCP-D and DCP-A-grades relevant for their use in tooth pastes have often been described in the pertinent literature and patents. DCP-grades intended for use in tooth pastes are more especially required to have the properties set forth for these products in the specification of the Toilet Goods Association (T.G.A. No. 35). In addition to this, the art is aware of further DCP-D and DCP-A-testing methods permitting the products to be evaluated for their properties relevant for their use in tooth pastes. These methods have partially been so improved that qualitative results can also be determined quantitatively.

It is also known that DCP-D of the kind used as a cleaning agent in tooth pastes can be stabilized against hydrolysis and loss of water of crystallization by means of dimagnesium phosphate-trihydrate (DMP) and sodium pyrophosphate (cf. German Specification DE-C 2,648,061).

To this end, a calcium compound and phosphoric acid are reacted while stirring in a reactor provided with a propeller mixer rotating at a speed of 2000 rpm, at a pH between 2 and 4, and—by reacting a magnesium salt solution with phosphoric acid—DMP is precipitated on the DCP-D obtained. Sodium pyrophosphate may be added as a stabilizer to the precipitating bath or dried product during grinding. The final product is ultimately separated, washed, dried and ground.

These conventional cleaning agents have an adsorptive power of 40 to 60 g $H_2O$/100 g cleaning agent; as a natural result and depending on the nature and kind of the particular thickener used, standard tooth pastes contain the cleaning agent in a concentration of 40 to 50 wgt %, corresponding to a density of the tooth paste of about 1.5 g/ml. A paste formulation typical of the most recent state in this art is indicated in Table 2 below, Example 6.

We have now unexpectedly found that tooth pastes containing a DCP-D cleaning agent having an adsorptive power of more than 60 g $H_2O$/100 g cleaning agent, preferably 100 to 135 g $H_2O$/100 g cleaning agent, have a density lower than that of conventional pastes but the same consistency as the latter.

In accordance with this invention, the cleaning agent should be stabilized with DMP and consist of 90 to 98 wgt % $CaHPO_4 \cdot 2H_2O$, the balance being $MgHPO_4 \cdot 3H_2O$, and sodium pyrophosphate.

It is also preferable for the present cleaning agent to have a particle size of at most 100 $\mu$m and the following particle size distribution: at least 99.95%<75 $\mu$m, 99.00%<44 $\mu$m, 50.00%<20 $\mu$m.

It is also an unexpected result which the ordinary artisan would not have expected that a cleaning agent having all of the properties hereinabove specified is obtainable by (a) introducing an aqueous suspension of 4 to 30 wgt % $CaCO_3$, preferably 15 to 20 wgt %, into a reactor provided with a circulating means and additionally with a high speed mixer rotating at a speed of more than 3000 rpm, preferably 5000 to 8000 rpm, and circulating the said suspension, the $CaCO_3$ being precipitated $CaCO_3$ with a mean particle size of less than 10 $\mu$m;

(b) producing, with the aid of the said mixer, a turbulent stirring zone in the continuously circulated suspension;

(c) directly feeding into the said stirring zone phosphoric acid of more than 70 wgt % strength, preferably 83 to 85 wgt %, in an excess of at most 10 wgt %, preferably less than 5 wgt %, based on the formation of $CaHPO_4 \cdot 2H_2O$, while maintaining a temperature of less than 40° C., preferably 22° to 30° C.;

(d) introducing into the said stirring zone a quantity of an aqueous magnesium salt solution, e.g. of $MgCl_2$, sufficient for establishing a $MgHPO_4 \cdot 3H_2O$-content of 1 to 9.5 wgt % in the final product;

(e) adding sodium hydroxide solution, preferably a solution of 25 wgt % strength concurrently with the said magnesium salt solution or subsequently until establishment of a pH of 6.0 to 6.9, preferably 6.3 to 6.4; and (f) separating the entire quantity of precipitate obtained, washing it and drying it at temperatures lower than 40° C.

The present process compares favorably with the prior art methods for making stabilized DCP-D in the improvement which comprises using, as the calcium carbonate, precipitated calcium carbonate having a mean particle size of at most 20 $\mu$m; circulating the calcium carbonate suspension in the reactor; producing a turbulent stirring zone in the said circulated suspension by means of a high speed mixer rotating at a speed of more than 3000 rpm; and introducing directly into the said stirring zone the phosphoric acid and subsequently the magnesium salt solution.

Apart from the fact that DCP-D so made is obtained in the particle size targeted so that it is not necessary for it to be initially ground, only as little as about 33% DCP-D feed material is required to be used, instead of heretofore 48% DCP-D, for obtaining a paste of sufficient viscosity. Various paste formulations are exemplified hereinafter. The use of the cleaning agent of this invention in feed quantities smaller than heretofore naturally results in pastes of lower density (about 1.3 g/ml). Lower density means a larger volume per unit weight and this is clearly an economically beneficial effect bearing in mind that tooth pastes are customarily sold by volume rather than by weight. The reduction of the paste density from 1.5 to 1.3 corresponds to an increase in volume of more than 15%, based on the unit weight. In other words: 115 tubes tooth paste formulated in accordance with this invention are obtained with the quantity heretofore necessary for obtaining 100 tubes tooth paste containing conventional DCP-D.

The following Examples illustrate the invention which is naturally not limited thereto.

Cleaning agent specimens of this invention were initially prepared in two experiments:

EXPERIMENT I 5000 g fine-particulate, precipitated ®"SCHÄFER Cl" (this is a registered Trade Mark of Schäfer Dietz company/Lahn, Federal Republic of Germany) calcium carbonate having a mean particle size of less than 5 μm in 27 liter water was introduced into, and circulated in, a 50 l-double jacket glass reactor which was provided with a circulating pump, namely a pressure membrane pump, and a high speed ®"ULTRA-TURRAX" (this is a registered Trade Mark of Janke and Kunkel company, Staufen im Breisgau, Federal Republic of Germany) mixer functioning in accordance with the rotorstator-principle. By means of the said high speed mixer rotating at a speed of 8000 rpm a turbulent stirring zone was established in the said circulated suspension and 7500 g phosphoric acid of 84.5% strength was directly metered into the said zone using a dosing pump. The excess of $H_3PO_4$, based on DCP-D, was about 3%. The reaction temperature was maintained at 23° C. by cooling. After the phosphoric acid had been added, the stirring zone was fed with a 33% $MgCl_2$-solution which was used in a quantity equivalent to the formation of 5.2 wgt % $MgHPO_4 \cdot 3H_2O$. Next, the reaction mixture was admixed with a 25% sodium hydroxide solution until a pH of 6.3 to 6.4 was found to have established. 88 g $Na_4P_2O_7$ was ultimately added as a second stabilizer.

The DCP-D I so obtained was finally separated from mother liquor on a vacuum suction filter, washed and dried.

EXPERIMENT II

The procedure was substantially the same as in Experiment I, but a suspension of 1475 g precipitated ®"SOCAL P2" (this is a registered Trade Mark of Solvay GmbH., SolingenOhligs, Federal Republic of Germany) calcium carbonate having a mean particle size of 4 μm in 30 l water was introduced into, and circulated in, the reactor.

The mixer rotating at a speed of 5000 rpm was fed initially with 2000 g $H_3PO_4$ of 84% strength and then with 275 g of a 33% $MgCl_2$-solution and 620 g NaOH, and a pH of 6.4 was established.

2550 g DCP-D II (about 95% of the theoretical yield) which was additionally stabilized in known manner by admixing it with 22 g $Na_4P_2O_7$, was obtained.

The chemical and physical properties relevant for the use of the DCP-D I and DCP-D II-grades in tooth pastes are indicated in Table 1. The corresponding properties of a commercial DCP-D III-grade once in standard form and once ground are given for the purpose of comparison, in order to demonstrate the influence of the particle size upon the power of adsorbing water (water adsorption). As can be seen, grinding the material (i.e. reducing its mean particle size from 16.0 to 7.1 μm) permits the water adsorption rate to be increased insignificantly only, from 52 to 58, i.e. to a value which is far from approaching the values determined for the DCP-D I and DCP-D II-grades of this invention, despite the fact that these latter present a significantly larger mean particle size between 12.0 and 17 μm.

The usefulness of a DCP-D as a cleaning agent in tooth paste is greatly determined by its stability in an aqueous medium, which should substantially avoid the loss (release) of water of crystallization and hydrolytic decomposition with formation of hydroxyl apatite, $Ca_5(PO_4)_3OH$, and orthophosphoric acid. These two reactions are undesirable as they affect the consistency and/or pH-value of the tooth paste which frequently undergoes phase separation and may ultimately become hard as concrete.

The tendency to release water of crystallization can be determined qualitatively with the aid of the so-called glycerol-set-test (T.G.A. No. 35). This test is run on a slurry which consists of approimately equal parts of a glycerol/water-blend and DCP-D, and is heated for 30 minutes in a boiling water bath.

The stability is deemed to be sufficient if the cooled slurry is still freely flowable. In order quantitatively to identify the loss of water of crystallization, the DCP-D is separated, washed and dried, and the loss on ignition is determined at 800° C. The value so obtained permits conclusions to be drawn as to the loss of water of crystallization which actually occurred due to the heat treatment, by comparing it with the loss on ignition of the untreated product. As can be seen from Table 1, the agents of this invention compare favorably with the commercially available product.

The stability to hydrolysis is tested on an aqueous DCP-D-suspension which is admixed with about 6.5 wgt % NaF, based on the DCP-D used, in order to accelerate the formation of hydroxyl apatite or fluorapatite. DCP-D is deemed to be sufficiently stable if an aqueous suspension of it has a pH not lower than 3 at 60° C. after 4 hours. In order quantitatively to identify the hydrolysis, the orthophosphoric acid formed after 4 hours was determined alkalimetrically. The values indicated in Table 1 show that the present agents at least match the quality of the commercial product.

The DCP-D I and DCP-D II-grades of this invention and the commercial DCP-D III-grade and DCP-D III-grade ground were used for making tooth pastes by processes known to the artisan, the formulations of which are indicated in Table 2.

The properties of the individual tooth pastes relevant for their practical use are indicated in Table 3.

As can be seen, the tooth pastes made with the present DCP-D-grades (Examples 1 to 5) have densities between 1.32 and 1.37 g/l which are distinctly lower than the density of the paste made from the commercial product (Example 6, density=1.52 g/ml).

The DCP-D-grades of this invention (Example 1 to 4) have an abrasiveness, determined by the copper abrasion-method (based on standard DCP-D with the arbitrary abrasion index=100) which is approximately 50% that of the commercial product (Example 6).

Example 5 shows that it is possible for the abrasiveness to be increased up to the value of commercially available DCP-D-material using the present products in admixture with minor quantities of commercially available anhydrous dicalcium phosphate (DCP-A).

In order to ensure a satisfactory prophylactic effect against caries, it is invariably necessary for whatever tooth paste to be sufficiently compatible with fluorine, i.e. the fluorine initially added to the tooth paste—customarily as $Na_2PO_3F$ in a DCP-paste—should remain fairly soluble. It is generally accepted art that the so-called fluorine-retention which naturally depends on the storage period, should in each case be determined at ambient temperature (20° C.) and increased temperature (43° C.). The fluorine-retention values in Table 3 show that the tooth pastes made in accordance with this invention compare very favorably with standard pastes. The viscosity values determined under identical temperature/time-conditions for the various DCP-D-grades are quite normal. The pastes made in accordance with this invention were additionally evaluated for their outer appearance but could not be found to compare unfavorably with the standard paste.

We claim

1. A tooth paste of dicalcium phosphate dihydrate containing a cleaning agent consisting essentially of dicalcium phosphate dihydrate having an adsorptive power of more than 60 g $H_2O$/100 g cleaning agent.

2. A tooth paste as claimed in claim 1, wherein the cleaning agent further consists of 90 to 98 wgt % $CaHPO_4 \cdot 2H_2O$, the balance being $MgHPO_4 \cdot 3H_2O$ and sodium pyrophosphate.

3. A tooth paste as claimed in claim 1, wherein the cleaning agent has a maximum particle size of 100 μm and a particle size distribution of at least 99.95% <75 μm, 99.0% <45 μm, and 50.0% <20 μm.

4. A cleaning agent of dicalcium phosphate dihyhrate characterized by an adsorptive power of more than 60 g $H_2O$/100 g cleaning agent.

5. A cleaning agent as claimed in claim 4, consisting of 99 to 98 wgt % $CaHPO_4 \cdot 2H_2O$, the balance being $MgHPO_4 \cdot 3H_2O$ and sodium pyrophosphate.

6. A cleaning agent as claimed in claim 4, characterized by a particle size of at most 100 μm and a particle size distribution of at least 99.95% <75 μm, 99.0% <45 μm, and 50.0% <20 μm.

7. A tooth paste containing metal phosphate as a cleaning agent, wherein the cleaning agent consists of 90 to 98 wgt % $CaHPO_4 \cdot 2H_2O$, the balance being $MgHPO_4 \cdot 3H_2O$ and $Na_4P_2O_7$, the cleaning agent having an adsorptive power of more than 60 g to 135 g $H_2O$/100 g cleaning agent, the cleaning agent having a particle size distribution of at least 99.95 wgt % <75 μm, 99.0 wgt % <45 μm, and 50.0 wgt % <20 μm.

TABLE 1

| Chem./physical-properties | | | DCP-D 1 | DCP-D II | DCP-D III | DCP-D III (ground) |
|---|---|---|---|---|---|---|
| Particle size | | | | | | |
| (a) Wet screening | <75 μm | (wgt. %) | 99.98 | 99.8 | 99.98 | 99.98 |
| | <45 μm | (wgt. %) | 99.9 | 99.8 | 99.6 | 99.9 |
| (b) Coulter-Counter | 90% < | (μm) | 17.4 | 22.0 | 29.3 | 12.3 |
| | 75% < | (μm) | 13.4 | 18.8 | 20.8 | 8.4 |
| | 50% < | (μm) | 10.0 | 15.0 | 11.9 | 6.0 |
| | 25% < | (μm) | 7.4 | 10.7 | 6.3 | 4.2 |
| | 10% < | (μm) | 5.5 | 7.8 | 3.9 | 3.1 |
| Mean particle size | | (μm) | 12.0 | 17.0 | 16.0 | 7.1 |
| Water adsorption (g $H_2O$/100 g DCP-D) | | | 134 | 120 | 52 | 58 |
| Apparent density Germ. Ind. Stand DIN 53 194 | | (g/l) | 530 | 540 | 980 | 860 |
| pH-value (20% suspension) | | | 7.5 | 7.5 | 7.4 | 7.4 |
| Loss on ignition at 800° C. | | (wgt. %) | 27.6 | 26.9 | 25.3 | 25.2 |
| Glycerol-Set-Test (T.G.A.) | | | good | good | good | good |
| Loss on ignition after Glycerol-Set-Test | | | 24.5 | 24.8 | 21.0 | 20.6 |
| pH-decrease-Test t to pH <3 | | (min) | >240 | >240 | >240 | >240 |
| (mg $H_3PO_4$/25 g DCP-D) in 240 min | | | 550 | 560 | 530 | 540 |

TABLE 2

| Contituents | weight parts | | | | | |
|---|---|---|---|---|---|---|
| | Ex. 1 | Ex. 2 | Ex. 3 | Ex. 4 | Ex. 5 | Ex. 6 |
| DCP-D I | 33.0 | 33.0 | 33.0 | — | 32.0 | — |
| DCP-D II | — | — | — | 34.5 | — | — |
| DCP-D III | — | — | — | — | — | 48.0 |
| DCP-A | — | — | — | — | 2.0 | — |
| Water | 39.84 | 33.84 | 37.84 | 36.54 | 36.84 | 24.84 |
| Glycerol (99% strength) | 11.0 | — | 24.0 | 24.0 | 24.0 | 11.0 |
| Sorbitol (70% strength) | 11.0 | 28.0 | — | — | — | 11.0 |
| Na-Lauryl sulfate | 2.0 | 2.0 | 2.0 | 2.0 | 2.0 | 2.0 |
| Carboxymethylcellulose | 1.0 | 1.0 | 1.0 | 0.8 | 1.0 | 1.0 |
| Aroma | 1.0 | 1.0 | 1.0 | 1.0 | 1.0 | 1.0 |
| Na-Monofluoro phosphate | 0.76 | 0.76 | 0.76 | 0.76 | 0.76 | 0.76 |
| Na-Saccharinate | — | — | 0.2 | — | — | — |
| Acesulfame | 0.2 | 0.2 | — | 0.2 | 0.2 | 0.2 |
| K-Sorbate | 0.2 | 0.2 | 0.2 | 0.2 | 0.2 | 0.2 |

TABLE 3

| | Ex. 1 | Ex. 2 | Ex. 3 | Ex. 4 | Ex. 5 | Ex. 6 |
|---|---|---|---|---|---|---|
| Abrasiveness index | 50 | 60 | 55 | 45 | 100 | 115 |
| Density (g/ml) | 1.32 | 1.33 | 1.33 | 1.37 | 1.36 | 1.52 |
| Fluorine-Retention 20° C./43° C. (mg/kg F) | | | | | | |
| immediate | 940/— | 950/— | 925/— | 940/— | 970/— | 790/— |
| after 30 days | 890/760 | 900/780 | 910/740 | 880/820 | 950/860 | 750/470 |
| after 90 days | 820/610 | 850/700 | 790/560 | 870/760 | 940/760 | 640/280 |
| after 180 days | 800/550 | 830/640 | 740/530 | 850/690 | 870/700 | 610/140 |
| Viscosity 20° C./43° C. (mPas · $10^3$) | | | | | | |
| immediate | 112/— | 114/— | 113/— | 124/— | 116/— | 126/— |
| after 30 days | 121/123 | 124/127 | 119/127 | 128/132 | 122/126 | 131/134 |
| after 90 days | 127/131 | 130/135 | 127/132 | 135/140 | 127/135 | 137/142 |
| after 180 days | 130/136 | 132/140 | 131/137 | 138/145 | 132/141 | 140/146 |

* * * * *